United States Patent
Hanyu et al.

(10) Patent No.: US 7,235,253 B2
(45) Date of Patent: Jun. 26, 2007

(54) POWDER CONTAINING PHYSIOLOGICALLY ACTIVE PEPTIDE

(75) Inventors: Yoshinobu Hanyu, Kobe (JP); Mariko Okada, Ashiya (JP); Chihiro Shindo, Kobe (JP); Satoshi Nishimuro, Kobe (JP); Tetsuo Yokoyama, Kobe (JP); Masato Horie, Kobe (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 508 days.

(21) Appl. No.: 09/994,773

(22) Filed: Nov. 28, 2001

(65) Prior Publication Data

US 2002/0058624 A1 May 16, 2002

Related U.S. Application Data

(62) Division of application No. 09/810,483, filed on Mar. 19, 2001.

(30) Foreign Application Priority Data

Mar. 21, 2000  (JP) ............................................ 2000-78775
Oct. 11, 2000  (JP) ........................................ 2000-310693
Jan. 24, 2001  (JP) .......................................... 2001-15904

(51) Int. Cl.
*A01N 25/34* (2006.01)
*A61N 9/48* (2006.01)
*A61K 9/28* (2006.01)
*A61K 9/30* (2006.01)
*A61K 9/36* (2006.01)

(52) U.S. Cl. ........................ 424/408; 424/451; 424/474; 424/475; 424/476; 424/479; 424/480; 424/482; 514/238; 514/241; 514/247; 514/252

(58) Field of Classification Search ................ 424/408, 424/451, 474, 475, 476, 479, 480, 482; 514/238–241, 514/247, 252; 435/6, 91.2, 173.5, 173.6, 435/173.7
See application file for complete search history.

(56) References Cited

U.S. PATENT DOCUMENTS

| | | | |
|---|---|---|---|
| 4,963,367 A | 10/1990 | Ecanow | |
| 4,976,968 A | 12/1990 | Steiner | |
| 5,096,885 A | 3/1992 | Pearlman et al. | |
| 5,334,162 A | 8/1994 | Harris | |
| 5,607,915 A | 3/1997 | Patton | |
| 5,654,278 A | 8/1997 | Sorensen | |
| 5,705,482 A | 1/1998 | Christensen et al. | |
| 5,763,439 A | 6/1998 | Shigehara et al. | |
| 5,839,443 A | 11/1998 | Rose et al. | |
| 5,898,030 A | 4/1999 | Samartani | |
| 5,955,448 A | 9/1999 | Colaco et al. | |
| 5,997,848 A | 12/1999 | Patton et al. | |
| 6,017,549 A | 1/2000 | Knight et al. | |
| 6,103,697 A | * 8/2000 | Bergstrand et al. ........... | 514/14 |
| 6,117,434 A | * 9/2000 | Oyama et al. ............... | 424/401 |
| 6,156,343 A | * 12/2000 | Morita ........................ | 424/474 |
| 6,284,282 B1 | 9/2001 | Maa et al. | |
| 6,335,316 B1 | 1/2002 | Hughes et al. | |
| 6,455,053 B1 | 9/2002 | Okada et al. | |

FOREIGN PATENT DOCUMENTS

| | | | |
|---|---|---|---|
| JP | 7-79364 | 7/1985 | |
| JP | 7-179364 | 7/1995 | |
| JP | 7-188060 | 7/1995 | |
| JP | 7-188061 | 7/1995 | |
| JP | 10504531 | 5/1998 | |
| JP | 10505591 | 6/1998 | |
| JP | 10507183 | 7/1998 | |
| JP | 10511965 | 11/1998 | |
| WO | 95/35116 | 12/1995 | |
| WO | WO 97/39768 | * 10/1997 | ............. 204/182.8 |

OTHER PUBLICATIONS

An English Language abstract of JP 7–179364.
An English Language abstract of JP 7–188060.
An English Language abstract of JP 7–188061.
English Language abstract of W.I.P.O. No. 95/35116.
English Language abstract of W.I.P.O. No. 96/21461.
English Language abstract of W.I.P.O. No. 96/11704.
English Language abstract of W.I.P.O. No. 96/05809.

* cited by examiner

*Primary Examiner*—Kenneth R. Horlick
*Assistant Examiner*—Joyce Tung
(74) *Attorney, Agent, or Firm*—Greenblum & Bernstein, P.L.C.

(57) ABSTRACT

A method is disclosed for stabilizing a physiologically active peptide in a process of preparing a powder containing the physiologically active peptide by drying an aqueous liquid containing the physiologically active peptide, wherein the method comprises adding to the aqueous liquid at least one compound selected from the group consisting of a nonionic surfactant, a water-soluble, nonionic, organic binder, hydrogenated lecithin, and mannitol.

2 Claims, 4 Drawing Sheets

POWDER CONTAINING PHYSIOLOGICALLY ACTIVE PEPTIDE

This application is a divisional of application Ser. No. 09/810,483, filed Mar. 19, 2001, which claims priority of Japanese Application Nos. 2000-78775, filed Mar. 21, 2000, 2000-310693, filed Oct. 11, 2000, and 2001-15904, filed Jan. 24, 2001. The entire disclosure of application Ser. No. 09/810,483 is considered as being part of the disclosure of this application, and the entire disclosure of application Ser. No. 09/810,483 is expressly incorporated by reference herein in its entirety.

FIELD OF THE INVENTION

The present invention relates to a physiologically active peptide-containing powder, and in particular to a physiologically active peptide-containing powder in which contamination by denatured peptides has been suppressed by stabilizing the physiologically active peptide and hereby preventing its denaturation from taking place in the process of forming a powder by drying an aqueous liquid containing the-physiologically active peptide. The present invention further relates to a physiologically active peptide-containing powder suitable for transpulmonary and transnasal administration by inhalation.,

BACKGROUND OF THE INVENTION

Administration of pharmaceutical products containing a physiologically active peptide have been made, so far, by injection. In this context, lyophilization has exclusively been employed in the preparation of such pharmaceutical compositions. Thus, for such pharmaceutical compositions, studies addressed to the stabilization of their active components, physiologically active peptides, have so far been focused on either the long-term storage stability of the physiologically active peptides in a dry state pharmaceutical compositions of the final products, or the storage stability of the physiologically active peptides in liquids which are prepared by dissolving the peptide-containing dry compositions. For example, stabilization of calcitonin solutions is disclosed in Japanese Unexamined Patent Publication Nos. H07-179364, H07-188060 and H07-188061, and stabilization of lyophilized growth hormone products is disclosed in Japanese Unexamined Patent Publication Nos. H10-504531, H10-511965 and H10-507183.

The reason why injection has been the sole way for administering physiologically active peptides is that, when they are, orally administered, physiologically active peptides are digested in the gastrointestinal tract. A practically applicable new route for administration, if established, would provide a great benefit to patients. Above all, in the case of active peptides requiring lifelong administration such as growth hormone and insulin, the conventional way of administration of injection has been giving patients inconvenience and pain. For these physiologically active peptides, therefore, establishment of a route of administration other than injection has been longed for by the patients.

On the other hand, those pharmaceutical compositions for systemic administration of a drug are under investigation that are intended either for transpulmonary absorption of a pharmacologically active ingredient by inhalation (referred to as an "inhalant composition" in the present specification) or for absorption of such an ingredient through the nasal mucous membrane by intranasal application, i.e. compositions for transnasal administration, as compositions utilizing other, new administration routes than those relied on by conventional pharmaceutical compositions such as injections, oral preparations, suppositories and the like. Inhalant compositions and compositions for transnasal administration are not directly injected into the body, but they are applied onto the surface of mucous membranes which are exposed to the air such as membranes of the respiratory tract. Therefore, their standards for microbiological quality control are not so strict as those for injections. Thus, they may be produced not only by a lyophilization apparatus but also by a fluid-bed granulation apparatus, a spray drying apparatus, or a spray-freeze drying apparatus. Concerning stabilization of active peptides in production steps of pharmaceutical compositions using a fluid-bed granulation apparatus, a spray drying apparatus, or a spray-freeze drying apparatus, it is reported that stabilization is attained by addition of an inhibitor of Maillard reaction (Japanese Unexamined Patent Publication No. H10-505591). However, it is preferable, if possible, that stabilization of a given active peptide in a production process should be achieved by means of approved pharmaceutical additives which are highly safe and have been used for years. This is because such an additive would allow to expect higher safety with regard to the final pharmaceutical product obtained. It is also required that the absorption and transferal to the blood of an physiologically active peptide is attained in sufficient efficiency.

The present invention has as its objectives to provide a method to improve stability of a physiologically active peptide in a process of producing a powder by drying an aqueous liquid containing the physiologically active peptide, as well as to provide a physiologically active peptide-containing powder produced by the method.

The present invention has as its further objectives to provide a physiologically active peptide-containing powder especially suited for absorption of the physiologically active peptide by inhalation, and to provide an inhalant composition.

SUMMARY OF THE INVENTION

For production of a powder containing a physiologically active peptide, the present inventors found that, in a process of preparing a powder containing a physiologically active peptide by drying an aqueous liquid containing the peptide, addition of certain compounds to the aqueous liquid remarkably increases the stability of the physiologically active peptides during the powder preparation. In addition, the present inventors also found that physiologically active peptides contained in the powder thus prepared are efficiently absorbed into the blood when the powder is transpulmonarily administered. The present invention was made on the basis of these findings.

Thus, the present invention provides a method for stabilization of a physiologically active peptide in a process of preparing a powder containing the physiologically active peptide by drying an aqueous liquid containing the physiologically active peptide, wherein the method comprises adding to the aqueous liquid at least one compound selected from the group consisting of a nonionic surfactant, a water-soluble, nonionic, organic binder, hydrogenated lecithin, and mannitol. In the method, a nonionic surfactant, a water-soluble, nonionic, organic binder, hydrogenated lecithin and mannitol serve as stabilizers in preparing a powder containing a physiologically active peptide from an aqueous liquid containing it. Thus, one or more of these compounds employed suppress denaturation such as dimer formation in the process of forming a powder from an aqueous liquid containing the peptide, thereby enabling to prepare a physiologically active peptide-containing powder which is substantially free of denatured peptides.

The present invention further provides a method for stabilization of a physiologically active peptide in a process of preparing a powder containing the physiologically active peptide by dring an aqueous liquid containing the physiologically active peptide, wherein the method comprises adding to the aqueous liquid mannitol and at least one compound selected from the group consisting of a nonionic surfactant, a water-soluble, nonionic, organic binder, and hydrogenated lecithin. This method enables, in addition to the above-mentioned benefit, to prepare a powder effecting especially efficient transpulmonary absorption of a physiologically active peptide.

In the above methods for stabilization, with regard to a nonionic surfactant or a water-soluble, nonionic, organic binder added to the aqueous liquid, the concentration range where they exhibit a potent stabilizing effect is 0.01–0.5% by weight for a nonionic surfactant and 0.01–1% by weight for a water-soluble, nonionic, organic binder. As for mannitol, it exhibits a potent stabilizing effect when added in an amount of 1–50 parts by weight per one part by weight of a physiologically active peptide.

In the above, it is more preferable that the nonionic surfactant is selected from the group consisting of polysorbate, polyoxyethylenehydrogenated castor oil, and a poloxamer (polyoxyethylene polyoxypropylene block copolymer: Pluronic).

Also in the above, the water-soluble, nonionic, organic binder is more preferably selected from the group consisting of polyvinylpyrrolidone, a water-soluble, nonionic, cellulose derivative and polyvinylalcohol.

Further, the water-soluble, nonionic, cellulose derivative is more preferably selected from the group consisting of hydroxypropylcellulose, hydroxyethylcellulose, and hydroxypropylmethylcellulose.

The effects of these stabilizers are remarkable in the above range, though they still have substantial effects somewhat outside the ranges. A still more preferable concentration range for a nonionic surfactant is 0.05–0.3% by weight, where a particularly potent stabilization effect is obtained. For a water-soluble, nonionic, organic binder, a concentration range still more preferable than the above is 0.02–0.5% by weight, where a particularly potent stabilization effect is obtained. As for hydrogenated lecithin, its stabilizing effect is particularly remarkable even at a concentration as low as 0.01% by weight. While its effect peaks at concentrations of 0.5–1% by weight, the effect remains still remarkable outside this range, and even at 2% by weight. Thus, the decline in its stabilizing effect is only limited even when its concentration goes up beyond the peak concentration. An upper limit concentration, therefore, is not clear over which hydrogenated lecithin would substantially lose its stabilizing effect. Its concentration, however, may be chosen as desired considering ease of handling in production of the pharmaceutical composition as there is no reason for using an unnecessarily large amount of hydrogenated lecithin insofar as it exhibits a sufficient effect as an additive. In general, the concentration of hydrogenated lecithin is preferably in the range of about 0.005–4% by weight, and more preferably in the range of 0.01–2% by weight. In light that the total amount of the powder administered is to be small insofar as it does not prevents easy handling, the weight proportion of a physiologically active peptide to mannitol is more preferably 1:1 to 1:40, further more preferably 1:1 to 1:30, still more preferably 1:1 to 1:20, and most preferably 1:1 to 1:10. For stabilization of an physiologically active peptide, any of the above stabilizers may be used alone, or two or more of them may be used in combination. When used in combination, they exhibit a still more remarkable stabilizing effect than when one of them is used alone, thus allowing to almost completely prevent the formation of denatured peptide such as a dimer.

The present invention is characterized in that its uses, in drying an aqueous liquid containing a physiologically active peptide, a certain group of compounds that were found to stabilize active peptides. The compounds can be used in a wide variety of specific methods for drying. In the above, example of methods for drying aqueous liquids include, but are not limited to, spray drying, lyophilization and spray-freeze drying, and, furthermore, a variety of methods which include a process of drying a solution by spraying it, such as drying performed in fluid-bed granulation, in a variety of coating method such as fluid-bed coating which allow to coat the surface of core particles, as well as drying performed in a granulation process in fluid-bed granulation involving coating of, or attachment of materials to, the surface of core particles.

Inhaled particles are more easily carried on the air flow deep into the respiratory system when their average size is 1–10 μm, and more preferably 2–5 μm. When given such a size, the particles of the physiologically active peptide-containing powder obtained in a stable form by one of the above methods are easily carried deep into the respiratory system by inhalation, allowing efficient and relatively long-lasting transferal of the physiologically active peptide into the circulating blood. Thus, the present invention further provides one of the above method in which the average size of the particles making up the powder is 1–10 μm, and more preferably 2–5 μm.

Examples of active peptides stabilized according to the present invention include calcitonins, insulins, growth hormones, erythropoietin, glucagon, somatostatin, somatostatin derivatives, interferons (α, β or γ), interleukins (I, II, III, IV, V VI or VII), superoxide dismutase, urokinase, proteases, tumor necrosis factors, colony-stimulating factors, kallikrein, lysozyme, fibronectin, as well as a variety of factors regulating growth or differentiation of cells such as insulin-like growth factors, epidermal growth factor, fibroblast growth factors, platelet-derived growth factor, nerve growth factor, hepatocyte growth factor, vasculogenesis factors, and anti-vasculogenesis factors. As active peptides share a common chemical structure that they consist of two or more amino acids linked by peptide bonds, the present invention is also applicable to a wide variety of other active peptides than those enumerated above. Moreover, it does not matter whether those peptides have been obtained by extraction from natural sauces or produced by application of genetic recombination technology, for such difference will not influence the basic physicochemical characters of the peptides. Among the above peptides, human growth hormone and human insulin are particularly preferred peptides in the present invention, for they are such peptides that patients have had to continue administering themselves by subcutaneous injection for a long period of time In addition to the above stabilizing methods, the present invention provides a method for preparation of a powder containing a physiologically active peptide. The method for preparation comprises forming a powder by drying an aqueous liquid containing a physiologically active peptide and a nonionic surfactant, a water-soluble, nonionic, organic binder, hydrogenated lecithin, and/or mannitol. By one or more of those stabilizers added to a physiologically active peptide, denaturation such as dimer formation is suppressed while the physiologically active peptide is in the process of forming a powder from an aqueous liquid containing the peptide. Thus, a physiologically active peptide-containing powder is prepared which is substantially free of denatured peptides.

The present invention further provides a method for preparation of a powder containing a physiologically active peptide, wherein the method comprises forming a powder by drying an aqueous liquid containing the physiologically active peptide, mannitol, and at least one compound selected from the group consisting of a nonionic surfactant, a water-soluble, nonionic, organic binder, and hydrogenated lecithin. This method for preparation, in addition to the above-mentioned benefit, provides a powder that effects especially efficient transpulmonary absorption of a physiologically active peptide.

In the method for preparation above, the nonionic surfactant is more preferably selected from the group consisting of polysorbate, polyoxyethylenehydrogenated castor oil, and a poloxamer (polyoxyethylene polyoxypropylene block copolymer: Pluronic). The water-soluble, nonionic, organic binder is more preferably selected from the group consisting of polyvinylpyrrolidone, a water-soluble, nonionic, cellulose derivative and polyvinylalcohol. The water-soluble, nonionic, cellulose derivative is more preferably selected from the group consisting of hydroxypropylcellulose, hydroxyethylcellulose, and hydroxypropylmethyl-cellulose.

In the method for preparation above, preferable ranges of the amount of the enumerated stabilizers when employed are the same as those mentioned for them in the method for stabilization of physiologically active peptides above. Therefore, a still more preferable concentration range for a nonionic surfactant is 0.05–0.3% by weight, and, for a water-soluble, nonionic, organic binder, a still more preferable concentration range is 0.02–0.5% by weight. As for hydrogenated lecithin, an upper limit concentration is not clear over which hydrogenated lecithin would substantially lose its stabilizing effect. Its concentration, however, may be chosen as desired considering ease of handling in production of the pharmaceutical composition as there is no reason for using an unnecessarily large amount of hydrogenated lecithin insofar as it exhibits a sufficient effect as an additive. In general, the concentration of hydrogenated lecithin is preferably in the range of about 0.005–4% by weight, and more preferably in the range of 0.01–2% by weight. As to mannitol, the weight proportion of a physiologically active peptide to mannitol is more preferably 1:1 to 1:40, further more preferably 1:1 to 1:30, still more preferably 1:1 to 1:20, and most preferably 1:1 to 1:10.

In the method for preparation above, example of methods for drying aqueous liquids include, but are not limited to, spray drying, lyophilization and spray-freeze drying, and fluid-bed granulation, as well as a variety of coating method, such as fluid-bed coating, which allow to coat the surface of core particles, and fluid-bed granulation involving coating of, or attachment of materials to, the surface of core particles.

In the method for preparation above, the average size of the particles making up the powder is preferably 1–10 μm, and more preferably 2–5 μm, when considering transpulmonary administration of a physiologically active peptide.

The range of physiologically active peptides formed into a powder by the method for preparation above is the same as already mentioned with regard to the method for stabilization.

The present invention further provides a powder containing a physiologically active peptide, wherein the powder is made up of particles comprising a physiologically active peptide and mannitol at a weight proportion of 1:1 to 1:50. In the powder, more preferably, the particles making up the powder further comprise, per one part by weight of the physiologically active peptide, at least one component selected from the group consisting of a nonionic surfactant in an amount of 0.05–3 parts by weight, a water-soluble, nonionic, organic binder in an amount of 0.05–6 parts by weight, and hydrogenated lecithin. Such a powder effects an efficient absorption of a physiologically active peptide through a mucous membrane deep in the respiratory system.

Considering reduction of the total weight of the powder inhaled per a predetermined amount of a physiologically active peptide to be administered, the weight proportion of a physiologically active peptide to mannitol in the particles above is more preferably 1:1 to 1:40, further more preferably 1:1 to 1:30, still more preferably 1:1 to 1:20, and most preferably 1:1 to 1:10. The amount of a nonionic surfactant is more preferably 0.25–1.8 parts by weight per one part by weight of a physiologically active peptide, in which range efficient absorption of a physiologically active peptide is attained while suppressing the amount of a nonionic surfactant employed. Likewise, the amount of water-soluble, nonionic, organic binder is more preferably 0.1–3 parts by weight per one part by weight of a physiologically active peptide.

In the above powder containing a physiologically active peptide, the average size of the particles making up the powder is preferably 1–10 μm, and more preferably 2–5 μm. By giving such an average size to its particles, the powder becomes easily carried deep into the respiratory system by inhalation, allowing more efficient absorption of the physiologically active peptide.

Method for preparation of the above powder containing a physiologically active peptide is not limited. The powder may be prepared, for example, by spray drying, spray-freeze drying or lyophilization.

The range of physiologically active peptides in the above powder containing a physiologically active peptide is the same as already mentioned with regard to the method for stabilization.

The present invention further provides an inhalant composition containing a physiologically active peptide, wherein the inhalant composition comprises above-mentioned particles containing a physiologically active peptide. The inhalant composition may simply be such particles containing a physiologically active peptide, or they may be either clusters consisting of such particles loosely associated with one another or composites consisting of such particles plus larger, inert carrier particles (e.g. lactose) onto the surface of which the former particles are loosely attached. Such loose clusters or composites are constructed in an extent of looseness that, at the time of inhaling the composition, they will be disintegrated upon release from an inhalation device by the flow of air and the each fine particle containing a physiologically active peptide will thereby be liberated from the clusters or carriers into a separate particle Preparation of such loose clusters or loose and coarse composite particles can be prepared by any of a variety of methods well known to those skilled in the art for bringing particles of the size of one to several μm making up a powder into a loose association with one another or into a loose association onto larger, inert carrier particles. Such loose clusters or loose and coarse composite particles are intended to increase flowability of the composition for improved ease of filling and accuracy of filling amount in a process in which a unit dose of the inhalant compositions is filled into each of predetermined containers like capsules employed in a inhalation device. Therefore, once put in a capsule, it is allowed that the whole or part of particles are liberated to separate particles by external agitation and thus forming a powder within the capsule.

Figure 1:
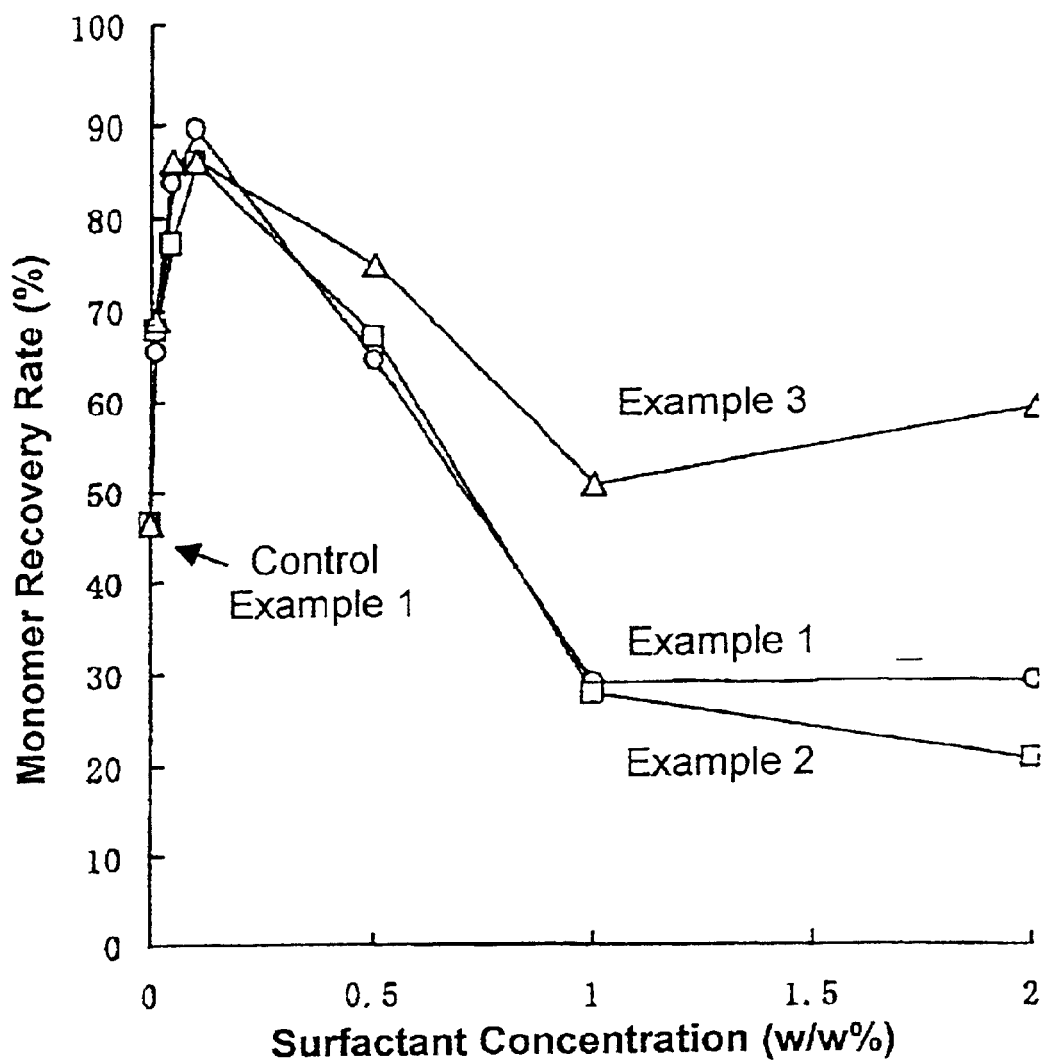
FIG. 1 is a graph illustrating the effect of nonionic surfactants.

DETAILED DESCRIPTION OF THE INVENTION

In the present invention, the term an "aqueous liquid containing a physiologically active peptide" includes not only at simple aqueous solution of a physiologically active peptide but also a solution of a physiologically active peptide further containing one or more other components that do not adversely affect the stability of the physiologically active peptide, e.g., buffering agents such as phosphates, pharmaceutically acceptable salts such as sodium chloride, and diluents such as sorbitol.

As the method for stabilization of the present invention stabilizes a physiologically active peptide dissolved in an aqueous liquid in a process of evaporating water from the aqueous liquid, its stabilization effect on a physiologically active peptide is not affected even by drying the physiologically active peptide coated on the surface of larger particles chemically inert to the active peptide, such as lactose and the like. Such inert particles serve as cores which carry on their surface a coat of the physiologically active peptide mixed with one or more stabilizing agents The powder of the present invention containing a physiologically active peptide is based on the discovery that a very efficient transpulmonary absorption is attained by employing particles comprising a physiologically active peptide and mannitol. Thus, any method of preparation may be chosen as desired for preparing such powder containing a physiologically active peptide. The method of the present invention for preparation of a powder containing a physiologically active peptide is based also on the discovery that mannitol has an effect of remarkably stabilizing a physiologically active peptide in the process of forming a powder by drying an aqueous liquid containing the peptide. Thus, drying of an aqueous solution containing a physiologically active peptide and mannitol may be performed by any conventional method as desired.

In the present invention, an example of particularly preferred physiologically active peptides is human growth hormone. In the present invention, the term "human growth hormone" means not only 22K hGH extractable from the pituitary of a human, which consists 191 amino acids and has a molecular weight of 22,125, but also 20K hGH, which lacks 15 amino acids corresponding amino acids 32–46. 20K hGH has a growth stimulating effect comparable to 22K hGH. In the present invention, the term "human growth hormone" means not only these natural types of human growth hormones, but also proteins which are produced by application of genetic recombination technology and having a substantially comparable effect to the natural human growth hormones. Examples of human growth hormone produced by application of genetic recombination technology include a N-terminal methionine-type hormone consisting 192 amino acids and variants which have part of their amino acids deleted, substituted, added or inserted and having a comparable activity to the natural types of human growth hormone.

EXAMPLES

When vigorously agitated in its aqueous solution, the molecule of growth hormone (GH), among active peptides, readily undergoes alteration in tertiary structure in contact with a gas-liquid interface, resulting in the loss of its monomer and leading to the formation of its dimer, polymer or insoluble aggregates, as well as to the formation of deamidation products. As the gas-liquid interface is expanded in a drying process such as spray drying, it is necessary, particularly in the case of GH, to manage to minimize its denaturation induced by this expansion of the interface in the process of forming GH into a powder. Studies were made as described below in search of a compound that stabilizes GH. In the Examples and Control Examples below, human growth hormone was chosen as a representative of active peptides.

The human growth hormone employed in the Examples and Control Examples below was a recombinant human growth hormone (in which N-terminal methionine had been selectively deleted enzymaticaly) which had the same amino acid sequence as the natural human growth hormone consisting of 191 amino acids (22K hGH). In addition, where the recombinant human growth hormone is identified as "Growject Injection 4 IU", it indicates that a pharmaceutical product (Growject Injection 4 IU: JCR pharmaceuticals, Co., Ltd.) was employed there. The composition of Grovject Injection 4 IU is as follows. Where the recombinant human growth hormone is specifically noted as a "bulk material", it indicates the pure recombinant human growth hormone (produced by BTG), which is free of any additives.

| r-hGH Injection (Growject Injection 4 IU): | |
|---|---|
| (Formula) | |
| r-hGH | 4 IU (1.7 mg) |
| Disodium hydrogenphosphate | 2.2 mg |
| Sodium dihydrogenphosphate | 0.35 mg |
| Sodium chloride | 1.0 mg |
| D-mannitol | 20.0 mg |

Tests will be described below which were performed by spray drying as a representative model of drying processes of an aqueous liquid containing a physiologically active peptide. The apparatus employed for spray drying was Spray Dryer SD-1000 (EYELA).

As an indicator of stabilization of the physiologically active peptide r-hGH, recovery rate of the physiologically active peptide monomer was employed, for it is considered to be the best indicator of stabilization of the physiologically active peptide. Calculation of recovery rate was done according to the following equation, based on the concentration of the physiologically active peptide in the aqueous liquid before drying (before spray drying) and the content of recovered active peptide in the solution prepared by reconstituting the obtained powder (spray dried product) to the initial volume Recovery rate of physiologically active peptide monomer (%)=$A_p/A_f \times 100$ where:

$A_p$=area of monomer peak on HPLC for spray dried product, and $A_f$=area of monomer peak on HPLC before spray drying.

Control Example 1

To each of fifteen vials of the r-hGH injection (Growject Injection 4 IU) was added 1.0 ml of purified water to completely dissolve the injection. The r-hGH solution thus obtained (15 vials: 15.0 ml) was spray-dried to obtain a dry powder. The conditions for spray drying in the Spray Dryer SD-1000 were adjusted as follows.
(Spray Drying Conditions)
Inlet temperature: 80° C.
Atomizing pressure: 150 kPa
Dry air low: 0.3 m³/min
Liquid feeder pump flow: 2.6 mL/min The conditions for HPLC for determination of the monomer content were as follows.
(HPLC Conditions)
Apparatus: LC10A (SHIMADZU CORPORATION)
Detector: UV (280 nm)
Analyzing column: TSK G3000SW$_{XL}$
Column temperature: Room temperature
Mobile phase: 50 mM sodium dihydrogenphosphate, 50 mM disodium hydrogenphosphate, 0.2 M sodium chloride.
Flow rate: 0.6 mL/min
Injection volume: 50 μL Control Example 2

Five sets of r-hGH injection (Grovject injection 4IU) vials, 15 vials per set, were provided. To each of the vials was added 1.0 mL of purified water to completely dissolve the injection. The r-hGH solution thus obtained (15.0 ml: 15 vials per set) was spray dried to obtain a dry powder. The conditions for spray drying in the Spray Dryer SD-1000 were different from those in Control Example 1 and adjusted as follows. The HPLC conditions for determination of the monomer content were the same as those in Control Example 1.
(Spray Drying Conditions)
Inlet temperature: 90° C.
Atomizing pressure: 100 kPa
Dry air flow: 0.2 m³/min
Fluid feeder pump flow: 2.6 mL/min Example 1

As solutions of a nonionic surfactant, aqueous solutions containing Tween 20 at different concentrations (concentration: 0.01, 0.05, 0.1, 0.5, 1.0 and 2.0 w/w %) were prepared. Fifteen vials of the r-hGH injection (Gromject Injection 4IU) were provided for each of the aqueous solutions containing Tween 20 at the different concentrations. The aqueous solutions containing Tween 20 at different concentrations were added to corresponding 15 vials, 1.0 mL each, and the injection was completely dissolved. Thus obtained r-hGH solutions containing Tween 20 at different concentrations (15.0 mL: 15 vials for each Tween 20 concentration) were spray-dried to obtain dry powders. The conditions for spray drying and HPLC were the same as those in Control Example 1.

Example 2

As solutions of a nonionic surfactant, aqueous solutions containing HCO-60 (polyoxyethylenehydrogenated castor oil) at different concentrations (concentration: 0.01, 0.05, 0.1, 0.5, 1.0 and 2.0 w/w %) were prepared. Fifteen vials of the r-hGH injection (Growject Injection 4IU) were provided for each of the aqueous solutions containing HCO-60 at different concentrations. The aqueous solutions containing HCO-60 at different concentrations were added to corresponding 15 vials, 1.0 mL each, and the injection was completely dissolved. Thus obtained r-hGH solutions containing HCO-60 at different concentrations (15.0 mL: 15 vials for each HCO-60 concentration) were spray-dried to obtain dry powders. The conditions for spray drying and HPLC were the same as those in Control Example 1.

Example 3

As solutions of a nonionic surfactant, aqueous solutions containing Pluronic F68 (polyoxyethylene(160) polyoxypropylene(30) glycol) at different concentrations (concentration: 0.01, 0.05, 0.1, 0.5, 1.0 and 2.0 w/w %) were prepared. Fifteen vials of the r-hGH injection (Growject Injection 4IU) were provided for each of the aqueous solutions containing Pluronic F68 at different concentrations. The aqueous solutions containing Pluronic F68 at different concentrations were added to corresponding 15 vials, 1.0 mL each, and the injection was completely dissolved. Thus obtained r-hGH solutions containing Pluronic F68 at different concentrations (15.0 mL: 15 vials for each Pluronic F68 concentration) were spray-dried to obtain dry powders. The conditions for spray drying and HPLC were the same as those in Control Example 1.

Example 4

As solutions of a water soluble, nonionic, organic binder, aqueous solutions containing Kollidone 17PF (polyvinylpyrrolidone: BASF) at different concentrations (concentration: 0.01, 0.05, 0.1, 0.5, 1.0 and 2.0 w/w %) were prepared. Fifteen vials of the r-hGH injection (Growject Injection 4IU) were provided for each of the aqueous solutions containing Kollidone 17PF at different concentrations. The aqueous solutions containing Kollidone 17PF at different concentrations were added to corresponding 15 vials, 1.0 mL each, and the injection was completely dissolved. Thus obtained r-hGH solutions containing Kollidone 17PF at different concentrations (15.0 mL: 15 vials for each Kollidone 17PF concentration) were spray dried to obtain dry powders. The conditions for spray drying and HPLC were the same as those in Control Example 1.

Example 5

As a water soluble, nonionic, organic binder, aqueous solutions containing Kollidone 12PF (polyvinylpyrrolidone: BASF) at different concentrations (concentration: 0.01, 0.05, 0.1, 0.5, 1.0 and 2.0 w/w %) were prepared. Fifteen vials of the r-hGH injection (Growject Injection 4IU) were provided for each of the aqueous solutions containing Kollidone 12PF at different concentrations. The aqueous solutions containing Kollidone 12PF at different concentrations were added to corresponding 15 vials, 1.0 mL each, and the injection was completely dissolved. Thus obtained r-hGH solutions containing Kollidone 12PF at different concentrations (15.0 mL: 15 vials for each Kollidone 12PF concentration) were spray-dried to obtain dry powders. The conditions for spray drying and HPLC were the same as those in Control Example 1.

Example 6

As a water soluble, nonionic, organic binder, aqueous solutions containing HPC-SSL (hydroxypropylcellulose: TOSOH) at different concentrations (concentration: 0.01, 0.05, 0.1, 0.5 and 1.0 w/w %) were prepared. Fifteen vials of the r-hGH injection (Growject Injection 4IU) were provided for each of the aqueous solutions containing HPC-SSL at different concentrations. The aqueous solutions containing HPC-SSL at different concentrations were added to corresponding 15 vials, 1.0 mL each, and the injection was completely dissolved. Thus obtained r-hGH solutions containing HPC-SSL at different concentrations (15.0 mL: 15 vials for each HPC-SSL concentration) were spray-dried to obtain dry powders. The conditions for spray drying and HPLC were the same as those in Control Example 1.

Example 7

As solutions of a nonionic surfactant, aqueous solutions containing Lecinol S-10E (hydrogenated lecithin: NIKKO CHEMICALS) at different concentrations (concentration: 0.01, 0.05, 0.1, 0.5, 1.0 and 2.0 w/w %) were prepared. Fifteen vials of the r-hGH injection (Growject Injection 4IU) were provided for each of the aqueous solutions containing hydrogenated lecithin at different concentrations. The aqueous solutions containing hydrogenated lecithin at different concentrations were added to corresponding 15 vials, 1.0 mL each, and the injection was completely dissolved. Thus obtained r-hGH solutions containing hydrogenated lecithin at different concentrations (15.0 mL: 15 vials for each hydrogenated lecithin concentration) were spray-dried to obtain dry powders. The conditions for spray drying and HPLC were the same as those in Control Example 1.

Example 8

Aqueous solutions were prepared which contained HPC-SSL (hydroxypropylcellulose) and a nonionic surfactant in combination as indicated in the following table.

TABLE 1

| Aqueous solution No. | Concentration of HPC-SSL (w/w %) | Nonionic surfactant and its concentration (w/w %) | |
|---|---|---|---|
| A | 0.05 | HCO-60 | 0.05 |
| B | 0.05 | Pluronic F68 | 0.05 |
| C | 0.05 | Pluronic F68 | 0.10 |
| D | 0.10 | HCO-60 | 0.05 |
| E | 0.10 | HCO-60 | 0.10 |

Fifteen vials of the r-hGH injection (Growject Injection 4IU) were provided for each of the aqueous solutions containing HPC-SSL and a nonionic surfactant in different combinations. The aqueous solutions were added to a corresponding set of 15 vials, 1.0 mL each, and the injection was completely dissolved. Thus obtained r-hGH solutions (15.0 mL: per set of 15 vials for each combination) were spray-dried to obtain dry powders. The conditions for spray drying were the same as in Control Example 2, and HPLC conditions were the same as those in Control Example 1.

<Results of Analysis>

FIG. 1 shows the results of HPLC analysis performed in Control Example 1 and Examples 1–3.

As shown in the figure, the nonionic surfactants at concentrations in certain ranges, respectively, remarkably increased the recovery rate of the monomer of physiologically-active peptide r-hGH in the process of powder preparation from its aqueous solutions. While the content of r-hGH monomer fell to the order of 40% during powder preparation in Control Example 1, which employed no nonionic surfactant, r-hGH monomer was maintained in Examples 1–3, in contrast at much higher recovery rate in the samples containing 0.01–0.5 w/w % nonionic surfactants in aqueous solutions. The figure also shows that the stabilizing effect of the respective nonionic surfactants peaked at their concentrations of somewhere around 0.1 w/w %. Though lacking actually measured values, it is also evident, for example, that the nonionic surfactants at about 0.3 w/w % have higher stabilizing effects than at 0.5 w/w %.

Figure 2:
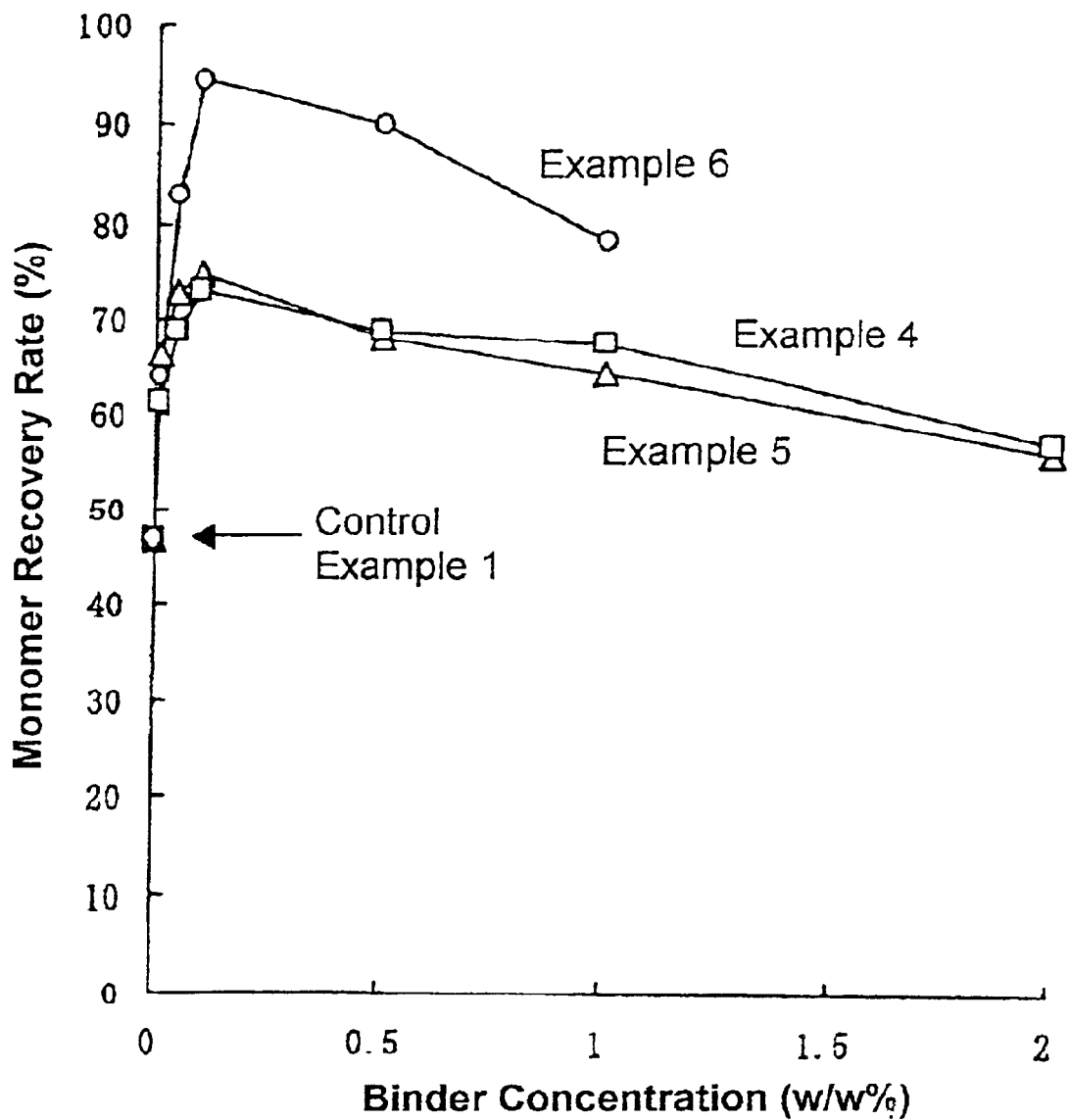
FIG. 2 is a graph illustrating the effect of water-soluble, nonionic, organic binders.

FIG. 2 shows the results of HPLC analysis performed in Control Example 1 and Examples 4–6.

As shown in the figure, the water-soluble, nonionic, organic binders markedly increased the recovery rate of the monomer of physiologically active peptide r-hGH in the process of powder preparation from its aqueous solutions. In Examples 4 (Kollidone 17PF) and 5 (Kollidone 12PF), improvement was noted at any of their concentrations tested. Their stabilizing effect was particularly potent up to a concentration of 1 w/w % and peaked at a concentration of 0.1 w/w %. As for Example 6 (hydroxypropylcellulose), stabilizing effect was still more remarkable than where the other binders were employed, showing a r-hGH recovery rate of about 95% at a concentration of 0.1 w/w %, where its effect peaked. In Example 6, hydroxypropylcellulose was tested only up to the concentration of 1 w/w %. However, it is largely evident that hydroxypropylcellulose would show a stabilizing effect even at 2 w/w %. This is because its effect at 1 w/w % was much higher than the effects of the other organic binders employed in Example 4 and 5 at the same concentration, and the decline in its effect by increasing its concentration beyond the peak is substantially not greater than the decline seen in the graphs for Examples 4 or 5.

Figure 3:
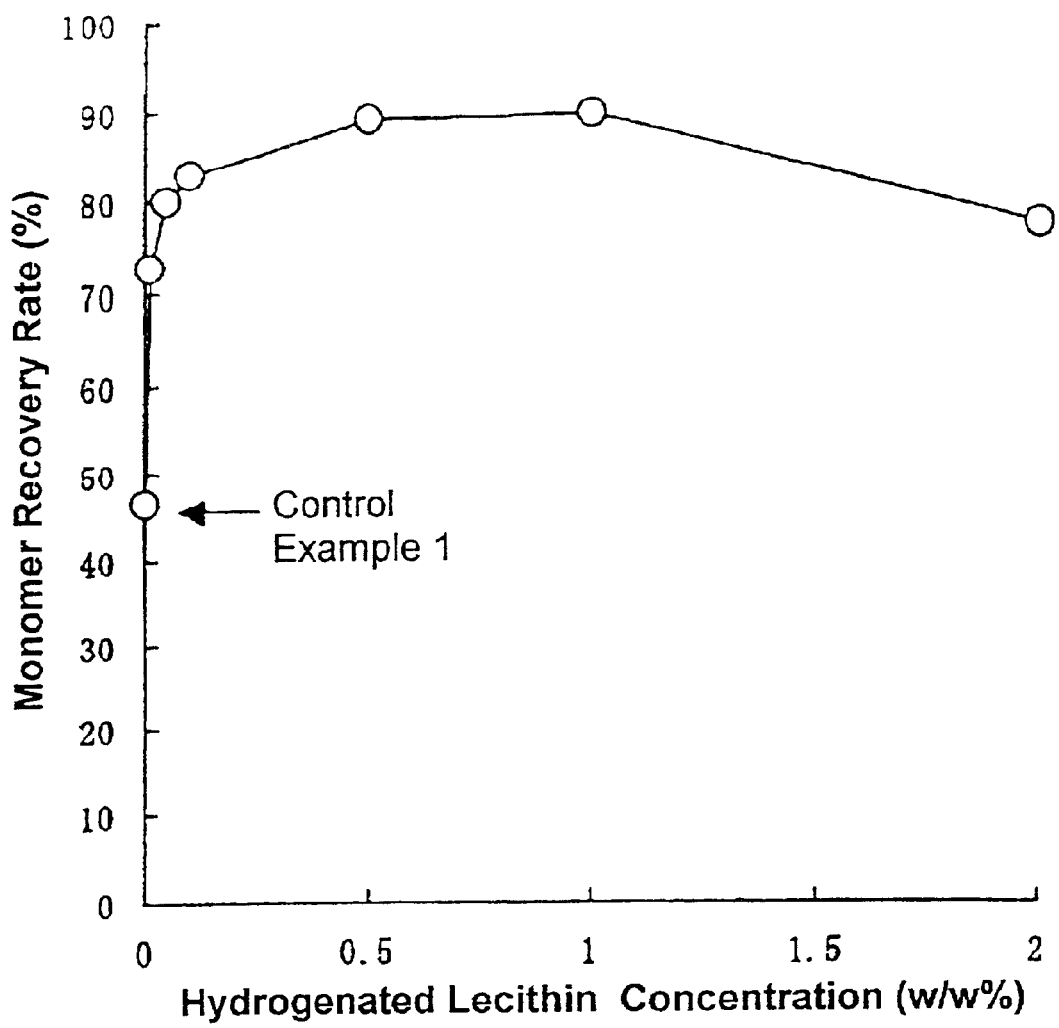
FIG. 3 is a graph illustrating the effect of hydrogenated lecithin.

FIG. 3 shows the results of HPLC analysis performed in Control Example 1 and Example 7.

As shown in the figure, hydrogenated lecithin, which was employed in Example 7, exhibited a remarkably potent stabilizing effect on r-hGH in any of the tested concentrations up to 2 w/w %. In particular, even at 0.01 w/w %, i.e. the lowest concentration tested, hydrogenated lecithin exhibited a stabilizing effect, raising the r-hGH recovery rate to more than 70%. Beyond that concentration and up to 0.2 w/w %, hydrogenated lecithin exhibited still higher stabilizing effects. While it seems from the figure that the effect of hydrogenated lecithin peaks at a concentration somewhere around 0.5–1 w/w %, its effect declines only slightly by increasing concentration beyond its peak. Therefore, there is no doubt that hydrogenated lecithin has a remarkable stabilizig effect in a concentration range much wider than tested above.

Following Table 2 shows the results of HPLC analysis for Comparison Example 2 and Example 8.

TABLE 2

| Aqueous solution No. | Concentration of HPC-SSL (w/w %) | Nonionic surfactant and its concentration (w/w %) | | Monomer recovery rate (%) |
|---|---|---|---|---|
| Control Example 2 | — | — | | 64.04 ± 1.30 |
| Example 8 A | 0.05 | HCO-60 | 0.05 | 99.20 ± 1.16 |
| Example 8 B | 0.05 | Pluronic F68 | 0.05 | 98.42 ± 0.61 |
| Example 8 C | 0.05 | Pluronic F68 | 0.10 | 97.96 ± 1.34 |
| Example 8 D | 0.10 | HCO-60 | 0.05 | 104.76 ± 0.68 |
| Example 8 E | 0.10 | HCO-60 | 0.10 | 104.81 ± 0.17 | n = 5, mean ± S.D.

As seen in Table 2, r-hGH was stabilized substantially perfectly in the process of forming its aqueous solution into a powder, by addition of both of hydroxypropylcellulose and a nonionic surfactant to the aqueous solution. This indicates that a combined use of both the water-soluble, nonionic organic binder—hydroxypropylcellulose—and a nonionic surfactant provides a higher stabilizing effect than by using them separately.

As seen from the results in Control Examples 1 and 2 and Examples 1–8, stability of physiologically active peptide r-hGH in a process of forming a powder from the aqueous solution of the physiologically active peptide is remarkably improved by adding to the solution; a nonionic surfactant such as polysorbate, polyoxyethylenehydrogenated castor oil and poloxamer and the like; a water-soluble, nonionic, organic binder such as hydroxypropylcellulose and polyvinylpyrrolidone and the like; or hydrogenated lecithin. Moreover, addition of two or more of these components in combination further improves the stability of the physiologically active peptide, leading to almost complete stabilization.

Example 9

Further studies were performed on the effect of mannitol, either employed alone or in combination with other additives.
(Materials)

As GH, a recombinant human growth hormone (r-hGH) bulk material was used. As stabilizers, D-mannitol, HPC-SSL and Pluronic F68 were used.
(Preparation of r-hGH Solution)

According to the following formulas, r-hGH and additives were weighed and dissolved in 15.0 mL of purified water to prepare spray solutions. As a control, r-hGH alone was dissolved in 15.0 mL of purified water to prepare a spray solution (Control Formula). In the formulas, "% by weight" in parentheses indicates the ratio of the weight of respective solid component to the weight of the solid components as a whole.

| (Formula M) | | |
|---|---|---|
| r-hGH | 29.25 mg | (6.5% by weight) |
| D-mannitol | 420.75 mg | (93.5% by weight) |
| Total | 450.00 mg | |
| (Formula M-HP) | | |
| r-hGH | 29.25 mg | (6.5% by weight) |
| D-mannitol | 405.00 mg | (90.0% by weight) |
| HPC-SSL | 15.75 mg | (3.5% by weight) |
| Total | 450.00 mg | |
| (Formula M-P) | | |
| r-hGH | 29.25 mg | (6.5% by weight) |
| D-mannitol | 405.00 mg | (90.0% by weight) |
| Pluronic F68 | 15.75 mg | (3.5% by weight) |
| Total | 450.00 mg | |

(Spray Drying)

As a spray dryer, EYELA SD-1000 Spray Dryer were used. Dry powders were prepared by spray-drying the above r-hGH solutions. The conditions for spray drying was as follows.
Inlet temperature: 90° C.
Dry air flow: 0.2 m³/min
Atomizing pressure: 100 kPa
Fluid feeder pump flow: 2.6 mL/min
(HPLC/Monomer Content Determination)

The conditions for HPLC for determination of r-hGH monomer were as follows.
Apparatus: LC10A (SHIMADZU CORPORATION)
Sample amount: about 0.02 g/0.5 mL purified water
Detector: UV (280 nm)
Analyzing column: TSK G3000SW$_{XL}$ (TOSOH)
Column temperature: Room temperature
Mobile phase: 0.1 M sodium dihydrogenphosphate, 0.1 M disodium hydrogenphosphate, 0.2 M sodium chloride.
Flow rate: 0.6 mL/min
Injection volume: 50 μL
(HPLC/ Determination of the Content of Deamidation Product)

The conditions for HPLC for determination of r-hGH deamidation products were as follows.
Apparatus: LC10A (SHIMADZU CORPORATION)
Sample amount: about 0.02 g/0.5 mL purified water
Detector: UV (280 nm)
Analyzing column: Protein C4 column (VYDAC, Cat. No. 214ATP54)
Column temperature: 45° C.
Mobile phase: 50 mM Tris-HCl (pH 7.5)/n-propanol (71:29) buffer
Flow rate: 0.5 mL/min
Injectionvolume: 50 μL
(SDS-polyacrylamide gel electrophoresis)
1) Preparation of Samples:

Solutions of about 0.04 mg/mL was prepared as samples. To each 10 μL of the solutions was added 10 μL of water and 20 μL of the sample buffer. As a standard sample, a solution of about 1.6 mg r-hGH bulk material/mL was prepared, to 10 μL of which was added 10 μL of water and 20 μL of the sample buffer.
2) Preparation of Electrophoresis buffer:
(A) An electrophoresis buffer for 10×SDS-PAGE was prepared by adding water to 30.3 g of Tris, 144 g of glycine and 10 g of SDS to make into volume of 1000 mL (for stock).
(B) An electrophoresis buffer for SDS-PAGE was prepared by adding 900 mL of water to 100 mL of the electrophoresis buffer for 10×SDS-PAGE.
(C) A 0.25 M Tris-HCl buffer (pH 6.8) was prepared by adding water to 30.25 g of Tris to make into volume of 800 mL, then adjusting the pH of the solution to 6.8 with 6 N hydrochloric acid, and making into volume of 1000 mL with water (preserved by freezing).
(D) A sample buffer for SDS-PAGE was prepared by adding water to 25 mL of 0.25 M Tris-HCl buffer (pH 6.8), 2 g of SDS, 5 g of sucrose and 2 mg of bromphenol blue (BPB) to make 50 mL.
3) SDS-PAGE Using the samples and the buffer described above, electrophoresis was carried out in a conventional manner at 20 mA/gel.
(Results)

The table below shows the results of the determination of the contents of r-hGH monomer and deamidation products in the r-hGH powders prepared above by freeze drying.

TABLE 3

| Formula | r-hGH Recovery Rate (%) | Content of Deamidation Products (%) |
|---|---|---|
| Control | 68.5 | 7.3 |
| M | 80.5 | 4.2 |
| M-HP | 91.4 | 4.5 |
| M-P | 88.4 | 4.7 |
| Bulk Material | — | 3.1 |

As evident from the Table 3, r-hGH monomer recovery rate was much higher in any of Formulas M, M-HP, M-P than in the control formula: while the recovery rate of r-hGH in the control formula was 68.5%, that was 80.5% in Formula M. In Formulas M-HP and M-P, r-hGH recovery rate was still higher. The content of deamidation products in any of the Formulas M, M-HP and M-P, which was lower than that in the control formula, was substantially not different from the proportion (3.1%) of deamidation products contained originally in the bulk material employed. In the control formula, in contrast, the content of deamidation products increased beyond two times. The analysis by SDS-PAGE also showed electrophoretic patters indicating that the purity of the peptide was higher in Formula M than in the control formula, and that the purity in Formula M-HP and M-P, in turn, was still higher than that in Formula M.

Example 10

Mannitol-containing r-hGH Powder for Transpulmonary Administration for in vivo Test According to the following formula, r-hGH, HPC-SSL and D-mannitol were weighed and dissolved in 90 mL of purified water to obtain a spray solution. In the formula, "% by weight" in parentheses indicates the ratio of the weight of respective solid component to the weight of the solid components as a whole. In the spray solution, the concentration of r-hGH, HPC-SSL and D-mannitol is 0.27% by weight, 0.14% by weight and 2.92% by weight, respectively. Spray drying and analyses were performed under the same conditions as in Example 9.

| (Formula) | | |
|---|---|---|
| r-hGH | 0.240 g | (8.0% by weight) |
| HPC-SSL | 0.129 g | (4.3% by weight) |
| D-mannitol | 2.631 g | (87.7% by weight) |
| Total | 3.000 g | |

The r-hGH dry powder prepared by spray drying was observed by optical microscopy. Six hundred particles were randomly chosen to measure their particle size. As a result, the particle size was found to be 2.84±0.83 μm (mean ±SD, n=600). The areas of the main peak (%) and the peak (%) for deamidation products were as follows.

TABLE 4

| | Area of Monomer Peak (%) | Area of Deamidation Products Peak (%) |
|---|---|---|
| Spray-dried Product | 95.5 | 4.5 |
| Standard | 96.6 | 3.4 |

<Pharmacokinetic Evaluation of GH Powder after Transpulmonary Administration to Rats>

The GH powder was administered to rats for pharmacokinetic evaluation. The same amount of the GH powder as transpulmonarily administered was dissolved in water and subcutaneously administered to rats to compare its pharmacokinetics with that of transpulmonarily administered GH.

(Test Animals)

Six male 9-week-old Wistar rats were used for transpulmonary and subcutaneous injection, respectively.

(GH Powder Tested)

The r-hGH powder obtained in Example 10 above was used.

(Administration of r-hGH)

After fasting for a full day and night, the rats of the transpulmonary administration group were anesthetized with urethane. Two mg/kg rat body weight of the r-hGH powder was placed in a transpulmonary administration device for rats (PennCentury). The powder was discharged into the lungs of the rats through the device's delivery tube inserted in the trachea by thrusting out 3 mL of air from a syringe connected to the device. The rats of the subcutaneous administration group were also fasted for a full day and night and then subcutaneously injected with the r-hGH powder suspended in purified water in an amount equivalent to 2 mg/kg rat body weight.

(Blood Sampling and Processing)

Blood sampling was performed just before the administration of r-hGH and then 0, 15, 30, 60, 120, 240, 480 and 1440 minutes thereafter. Blood was sampled from the cervical vein of restrained rats. Blood sampling volume was 300 μL at one time. Following each blood sampling, the same amount (300 μL) of physiological saline was injected into the cervical vein. Blood samples were let stand for one hour at room temperature and then overnight at 4° C., and centrifuged (15,000 rpm, 10 minutes, 4° C.) to separate the sera.

(Measurement of Blood r-hGH Concentration by GH-ELISA)

An anti-hGH rabbit polyclonal antibody raised by a conventional method was diluted and adjusted to the absorbance OD280 of 0.02 with a 0.05 M Tris buffer. The solution was placed, 100 μL each, in the wells of 96-well plates and incubated for two hours at 37° C. The plates were washed five times with a 0.01 M phosphate buffer (washing buffer). The wells of the plates were filled with a block solution (Block Ace: Dainippon Pharmaceutical Co., Ltd.) and let stand overnight at 4° C. The sera obtained above and r-hGH for a standard curve, respectively, were diluted as needed with 10×Block Ace aqueous solution and added to the wells of the washed plates, 100 μL each, and preincubated for 2 hours at 37° C.

Using the anti-hGH rabbit polyclonal antibody, a horseradish peroxidase (HRP)-conjugated anti-hGH rabbit polyclonal antibody was prepared in a conventional manner. The conjugated polyclonal antibody was diluted 50,000 times with 10×Block Ace aqueous solution and added to the wells of the washed plates, 100 μL each, and preincubated for 2 hours at 37° C. After washing, 100 μL each of TMB reagent (BIORAD) was added to the wells of the plates and allowed to react for 10 minutes at room temperature. The reaction was terminated by addition of 1 N sulfuric acid, and absorbance was measured at 450 nm. A calibration curve was created based on the absorbance for standard solutions, and the r-hGH concentrations in the samples were derived from their absorbance using the calibration curve.

(Results)

Table 5 and FIG. 4 show r-hGH concentrations in the blood after transpulmonary administration of the r-hGH powder or subcutaneous injection of the r-hGH suspension.

TABLE 5

| Time after Administration (min) | Blood r-hGH Concentration (ng/ml) Transpulmonary Administration | Subcutaneous Injection |
|---|---|---|
| 0 | 22.6 | 41.5 |
| 15 | 584.4 | 423.1 |

TABLE 5-continued

| Time after Administration (min) | Blood r-hGH Concentration (ng/ml) | |
|---|---|---|
| | Transpulmonary Administration | Subcutaneous Injection |
| 30 | 451.4 | 446.1 |
| 60 | 315.1 | 491.8 |
| 120 | 254.9 | 423.9 |
| 240 | 101.6 | 347.9 |
| 480 | 61.5 | 175.5 |
| 1440 | 34.7 | 51.3 |

Figure 4:
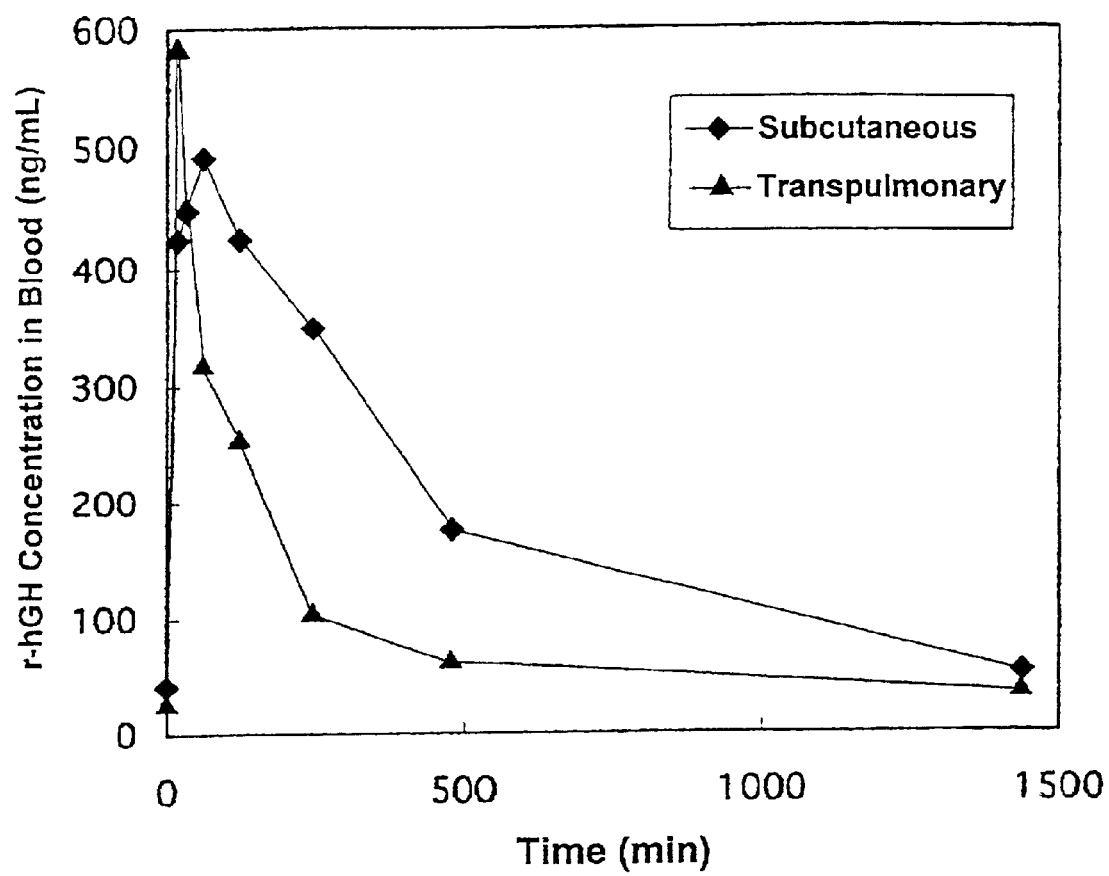
FIG. 4 shows blood concentration profiles of human growth hormone in rat after transpulmonary administration of a human growth hormone-containing powder and subcutaneous injection of the same amount of the powder.

As seen in Table 5 and FIG. 4, after transpulmonary administration of the r-hGH powder prepared in the above example, blood r-hGH concentration reached its peak of 584.4 ng/mL 15 minutes after the administration. The concentration then started to decline but still remained at 34.7 ng/mL even 1440 minutes after the administration. The AUC (area under the curve representing blood pharmacokinetics) up to 480 minutes after the administration was 128862 ng/mL·min for transpulmonary administration, whereas that was 255826 ng/mL·min for subcutaneous administration of the suspension containing the same amount of the powder. As the r-hGH was transferred to the blood in unexpectedly high efficiency after the subcutaneous injection of that composition, the blood concentration of r-hGH following transpulmonary administration was lower than that following its subcutaneous injection, except for a period immediately after pulmonary administration. However, the above results show that r-hGH absorption after transpulmonary administration of the composition was very high. In fact, the blood r-hGH concentration after the transpulmonary administration of the very composition was far higher than either of the blood r-hGH concentration after the transpulmonary administration or subcutaneous administration of the same amount of r-hGH suspension carried out in Control Example 3 below.

Control Example 3

According to the following formula, r-hGH and lactose were weighed and dissolved in 120 mL of purified water to obtain a spray solution. The concentration of r-hGH and lactose in the spray solution is 0.20 w/w % and 2.30 w/w %, respectively.

| (Formula) | | |
|---|---|---|
| r-hGH | 0.240 g | (8.0% by weight) |
| Lactose (monohydrate) | 2.760 g | (92.0% by weight) |
| Total | 3.000 g | |

The above spray solution was spray-dried under the following conditions.

Inlet temperature: 120° C.

Dry air flow: 0.2 $m^3$/min

Atomizing pressure: 100 kPa

Fluid feeder pump flow: 2.6 mL/min

Thus obtained stray-dried r-hGH powder was analyzed by the same method as described above for the content of monomer and deamidation products by HPLC, and subjected to SDS-PAGE. The area of the monomer peak and that of the peak deamidation products are as shown in the following table, and the SDS-PAGE pattern indicated high purity.

TABLE 6

| | Area for Monomer (%) | Area for Deamidation Products (%) |
|---|---|---|
| Spray-dried Product | 94.7 | 5.3 |
| Standard | 96.7 | 3.3 |

With this spray-dried product, r-hGH was transpulmonarily administered or subcutaneously injected to male 9-week-old Wistar rats, six animals per group, following the some dose and procedures as indicated in "Pharmacokinetic Evaluation of GH Powder after Transpulmonary Administration to Rats", and the pharmacokinetics for r-hGH was determined. The results are shown in the table below.

TABLE 7

| Time after Administration (min) | Blood r-hGH Concentration (ng/ml) | |
|---|---|---|
| | Transpulmonary Administration | Subcutaneous Injection |
| 0 | 5 | 6 |
| 15 | 147 | 46 |
| 30 | 129 | 52 |
| 60 | 85 | 62 |
| 120 | 70 | 75 |
| 240 | 58 | 71 |
| 480 | 48 | 21 |
| 1440 | 37 | 5 |

Natural human growth hormone, 22K hGH, is composed of 191 amino acids, with two S—S bonds within the molecule, whereas human insulin is composed of 51 amino acids and has two S—S bonds within the molecule. It is reasonably expected that transpulmonary absorption demonstrated above with the powders containing human growth hormone will occur also with human insulin, considering that the far smaller molecule of human insulin compared with human growth hormone will render the former more suitable for absorption through mucous membranes and that it shares a structural similarity with human growth hormone in light that they have two S—S bonds within their molecule. Likewise, successful transpulmonary absorption is expected to take place also with calcitonin (32 amino acids) and somatostatin (28 amino acids), which are roughly of half the size of human insulin, by forming them into the powder of the present invention.

The present invention enables to remarkably stabilize a physiologically active peptide in forming a powder by drying an aqueous solution containing the physiologically active peptide, thereby minimizing loss of the peptide in the process of powder formation. As it is done employing additives approved as safety ingredients in pharmaceutical products, the present invention also enables to produce a powder stably retaining a physiologically active peptide, without evoking unnecessary concerns on the safety of such a product due to employed additives. The present invention alto enables to provide physiologically active peptide-containing powder in which content of dimers or other denatured peptide is minimized, thereby making it easy to produce such types of pharmaceutical compositions that are adapted to be applied to mucous membranes in a powder form in order to introduce a drug into the circulating blood, e.g. pharmaceutical compositions for transnasal or transpulmonary administration. The present invention further enables to provide inhalant compositions which allow efficient transferal of growth hormone or insulin into the blood by transpulmonary administration.

What is claimed is:

1. A method of stabilization of a physiologically active peptide in a process of preparing a powder containing the physiologically active peptide, wherein the process comprises drying an aqueous liquid containing the physiologically active peptide to form a powder, wherein the method comprises adding to the aqueous liquid at least one compound selected from the group of a nonionic, organic, water soluble binder, and hydrogenated lecithin, and wherein the nonionic, organic, water-soluble binder is selected from polyvinylpyrrolidone, a water-soluble, nonionic cellulose derivative, and polyvinylalcohol; and wherein the water-soluble, nonionic cellulose derivative is selected from the group of hydroxypropylcellulose, hydroxyethylcellulose, and hydroxypropylmethylcellulose.

2. A method for preparation of a powder containing a physiologically active peptide from an aqueous liquid containing the physiologically active peptide while increasing the stability of the physiologically active peptide in the process of powder formation.

wherein the method comprises adding to the aqueous liquid containing the physiologically active peptide at least one compound selected from the group of a water-soluble, nonionic, organic binder, and hydrogenated lecithin, wherein the nonionic, organic, water-soluble binder is selected from polyvinylpyrrolidone, a water-soluble, nonionic cellulose derivative, and polyvinylalcohol, wherein the method comprises drying the liquid to form a powder; and wherein the water-soluble, nonionic cellulose derivative is selected from the group of hydroxypropylcellulose, hydroxyethlcellulose, and hydroxypropylmenthylcellulose.

* * * * *